(12) United States Patent
Wald et al.

(10) Patent No.: US 9,068,960 B2
(45) Date of Patent: Jun. 30, 2015

(54) METHOD AND COMPOSITION FOR DETECTING OXIDIZING SALTS

(71) Applicants: Lara Beth Wald, Perkins, OK (US); Gregory Charles Frye-Mason, Cedar Crest, NM (US)

(72) Inventors: Lara Beth Wald, Perkins, OK (US); Gregory Charles Frye-Mason, Cedar Crest, NM (US)

(73) Assignee: FLIR Systems, Inc., Wilsonville, OR (US)

( * ) Notice: Subject to any disclaimer, the term of this patent is extended or adjusted under 35 U.S.C. 154(b) by 309 days.

(21) Appl. No.: 13/650,820

(22) Filed: Oct. 12, 2012

(65) Prior Publication Data

US 2014/0106463 A1    Apr. 17, 2014

(51) Int. Cl.
*G01N 21/76* (2006.01)
*G01N 31/22* (2006.01)

(52) U.S. Cl.
CPC .............. *G01N 31/227* (2013.01); *G01N 31/22* (2013.01); *Y10T 436/173076* (2015.01); *Y10T 436/173845* (2015.01)

(58) Field of Classification Search
None
See application file for complete search history.

(56) References Cited

U.S. PATENT DOCUMENTS

| 3,117,837 | A | 1/1964 | Haase |
| 5,854,077 | A | 12/1998 | Wolfson et al. |
| 6,558,626 | B1 | 5/2003 | Aker et al. |
| 7,759,127 | B2 | 7/2010 | Rose et al. |
| 2010/0310424 | A1 | 12/2010 | Rose et al. |

OTHER PUBLICATIONS

Steinfeld, Jeffrey I., Explosive Detection: A Challenge for Physical Chemistry, Annu. Rev. Phys. Chem. 1998. 49: 203-232.
Brandner, J.D. et al., Vapor Pressure of Ammonium Nitrate, Journal of Chemical and Engineering Data, vol. 7, No. 2, Apr. 1962, pp. 227-228.
Lindgren, Per F., Trace Level Gaseous Hydrochloric Acid Measurement Standard Based on Sublimation of Ammonium Chloride, Anal. Chem. 1991, 63, 1008-1011.

*Primary Examiner* — Robert Xu
(74) *Attorney, Agent, or Firm* — McAfee & Taft

(57) ABSTRACT

The present invention provides methods for determining the presence of oxidizing salts. According to the current invention, analyte is collected on a swipe and subsequently heated to a temperature sufficient to release a detectable vapor phase component of the oxidizing salt. The vapor phase component passes reacts with a pH sensitive molecule. Reaction of the vapor phase product with the pH sensitive molecule produces a detectable change in response intensity.

26 Claims, 3 Drawing Sheets pH sensitive molecule Increase in Response Intensity.

FIG. 3

Log Scale: Maximum Percent Response for ANFO, Nitric Acid, Ammonium Nitrate and Urea Nitrate.

METHOD AND COMPOSITION FOR DETECTING OXIDIZING SALTS

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Oxidizing salts such as but not limited to ammonium nitrate, ammonium perchlorate, and urea nitrate have many industrial uses. Unfortunately, these strong oxidizing compounds may also be incorporated into homemade explosive devices. In particular, a high explosive known as ANFO (ammonium nitrate fuel oil) is easily prepared by combining ammonium nitrate with number two fuel oil or diesel fuel. A typical formulation for ANFO utilizes about two quarts of fuel oil and about fifty pounds of ammonium nitrate. Although commonly used in the mining industry, the simple process for preparing ANFO also makes it a ready formulation for terrorists. Thus, the ability to readily detect the presence of oxidizing salts will be beneficial to the detection and prevention of attacks using explosives based on oxidizing salts.

SUMMARY OF THE INVENTION

The current invention provides a method for detecting oxidizing salts. The method utilizes a pH sensitive molecule that undergoes a reversible reaction with an acid component of a vaporized oxidizing salt. The method of the current invention includes the steps of collecting a sample of an oxidizing salt. The collected sample is presented to a sensor assembly. The sensor assembly includes a solid substrate carrying the pH sensitive molecule; an excitation source, providing stimulating radiation at wavelengths selected for the type of pH sensitive molecule, and a light sensor monitoring the response intensity of the pH sensitive molecule to the stimulating radiation. Typically, the excitation source will operate at wavelengths between about 325 nm and about 700 nm, in one embodiment the excitation source operates at wavelengths between about 365 nm and about 410 nm. The collected oxidizing salt is heated to a temperature sufficient to evaporatively dissociate the oxidizing salt yielding evaporative dissociation compounds, i.e. the acid and base components, of the oxidizing salt. Following evaporative dissociation, a sufficient quantity of the acid component reacts with the pH sensitive molecule producing a change in response intensity of the pH sensitive molecule detectable by the light detector. Monitoring of the response level during the reaction of the pH sensitive molecule with the acid component wherein a response change of about three times a controlled response or more indicates the presence of an oxidizing salt.

In another embodiment, the present invention provides a method for determining the presence of oxidizing salt on a surface. According to this method, sampling material is brought into contact with a surface suspected of carrying an oxidizing salt selected from the group consisting of ammonium nitrate, urea nitrate, guanidine nitrate and ammonium perchlorate thereby collecting a sample from said surface. The sampling material is presented to a sensor assembly including a heater suitable for inducing evaporative dissociation of the oxidizing salt into its acid and base components. The sensor assembly includes a solid substrate carrying the pH sensitive molecule; an excitation source, providing stimulating radiation at wavelengths selected for the type of pH sensitive molecule, and a light sensor monitoring the response intensity of the pH sensitive molecule to the stimulating radiation. Typically, the excitation source will operate at wavelengths between about 325 nm and about 700 nm, in one embodiment the excitation source operates at wavelengths between about 365 nm and about 410 nm. Operation of the excitation source stimulates the pH sensitive molecule to produce a detectable response. During presentation of the sampling material to the sensor assembly, monitoring the response of the pH sensitive molecule to the stimulation with a light sensor suitable for detecting changes in response intensity. The step of heating releasing the evaporative dissociation components which pass into said sensor assembly. Once within the assembly at least one component reacts with the pH sensitive molecule. During the step of reacting at least one dissociation component with the pH sensitive molecule, the light sensor monitors the pH sensitive molecule for a change in response intensity when compared the intensity of response in the absence of a dissociation component thereby indicating the presence of an oxidizing salt on the sampled surface.

Still further, the present invention provides a detector assembly configured to detect trace amounts of evaporative dissociation compounds derived from an oxidizing salt. The detector assembly comprises a sensor assembly including a solid substrate carrying a pH sensitive molecule, an excitation source positioned to provide stimulating radiation to the pH sensitive molecule, a light sensor and a first heater suitable for adjusting the temperature of the sensor assembly. The excitation source is a pH sensitive molecule dependent capable of providing stimulating radiation at wavelengths between about 325 nm to about 700 nm to the pH sensitive molecule. The light sensor is suitable for detecting response intensity changes at wavelengths between about 360 nm and about 750 nm and positioned to monitor the response of the pH sensitive molecule to stimulation by the excitation source. The detector assembly also includes a sampling tip assembly in fluid communication with the sensor assembly. A second heater is associated with the sampling tip assembly. The second heater is suitable for maintaining the temperature of the sampling tip assembly at a temperature between about 90° and 350°. Additionally, the detector assembly includes a gas movement pump in fluid communication with the sampling tip and the sensor assembly. The gas movement pump configured to move vapors from the sampling tip assembly to and along the solid substrate of the sensor assembly.

DETAILED DISCLOSURE OF THE CURRENT INVENTION

Heating oxidizing salts, such as ammonium salts and urea salts, produces vapor phase basic and acidic components via a process known as evaporative dissociation (also known as thermal dissociation). For example, ammonium nitrate undergoes evaporative dissociation at temperatures below the melting point of 170° C. Evaporative dissociation of oxidizing salts produces the respective acid and basic components of the salt. Certain oxidizing salts are known to have significant vapor pressures at temperatures less than their melting points. For example, the vapor pressure of solid ammonium nitrate at 100° C. is 0.0024 mmHg and the vapor pressure increases to 1.17 mmHg at 165° C.

To demonstrate the ability to induce evaporative dissociation of an oxidizing salt, solid ammonium nitrate was subjected to evaporative dissociation at 170° C. Subsequently, downstream condensation of the resulting vapor components produced ammonium nitrate. For the six hour test period, the condensed, reformed ammonium nitrate showed only a 0.12% decomposition loss in the sample compared to the initial concentration of ammonium nitrate. The same experiment at 240° C. resulted in 15% of the sample decomposing into $NO_2$, $N_2O$, and NO, and well as $H_2O$ and $N_2$. Therefore, heating the solid ammonium nitrate above approximately 100° C. will induce evaporative dissociation of at least a portion of the solid ammonium nitrate to ammonia gas ($NH_3$) and nitric acid ($HNO_3$) while heating at temperatures greater than the compounds melting point decomposes the compound.

Thus, one can determine the presence of trace amounts of ammonium nitrate by heating the ammonium nitrate above 100° C. and subsequently detecting the presence of the vapor phase components. The temperature of evaporative dissociation for other oxidizing salts can be readily determined by standard industry methods. For example, ammonium nitrate is has a melting point of 170° and an extrapolated room temperature vapor pressure of $4.3 \times 10^{-7}$ torr. The temperature range suitable for inducing evaporative dissociation of ammonium nitrate is about 100° C. to about 170° C. Urea nitrate has a melting point of 133° C. and an extrapolated room temperature vapor pressure of $6.6 \times 10^{-7}$ torr. The temperature range suitable for inducing evaporative dissociation of urea nitrate is about 80° C. to about 133° C. Guanidine nitrate has a melting point of 213° C. and an extrapolated room temperature vapor pressure of $4.6 \times 10^{-14}$ torr. The temperature range suitable for inducing evaporative dissociation of guanidine nitrate is about 200° C. to about 225° C. Additionally, the evaporative dissociation temperature range for ammonium perchlorate is about 250-350° C.

The method of the current invention involves initially sampling a target area suspected to be contaminated with an oxidizing salt using a sampling material suitable for collecting oxidizing salts. Non-limiting examples of sampling materials suitable for collecting oxidizing salts from a target area include non-reactive polytetrafluoro ethylene swipes and other substrates substantially non-reactive with the suspected oxidizing salt and its components that have the ability to collect trace samples of oxidizing salts and will not decompose at the indicated operating conditions. Due to their ability to conform to irregular surfaces, polytetrafluoroethylene swipes are particularly suited for the method of the present invention. Subsequent heating of the sampling material, now carrying the oxidizing salts, will induce evaporative dissociation of the salt releasing the salt's acid and base components from the sampling material. Optionally, high volume collection of vapor and particles that can be heated may be carried out using a vortex sampler with a screen capture. Alternatively, the surface suspected of carrying oxidizing salts may be heated to release the dissociation components for collection by the sampling assembly.

The method of the current invention utilizes a sensor which incorporates a pH sensitive molecule. An example of a suitable pH sensitive molecule is 2-[5-methoxy-2-(4-phenyl-quinoline-2yl)-phenyl]-ethanol as represented by the following structure:

However, other suitable compounds include, but are not limited to: SNARF®-5F, 5-(and-6)-carboxylic acid as represented by the following structure where the carboxylic acid group may be positioned at either the indicated 5 or 6 position,

SNARF®-4F, 5-(and-6)-carboxylic acid as represented by the following structure where the carboxylic acid group may be positioned at either the indicated 5 or 6 position,

5-(and-6)-carboxy SNARF®-1, as represented by the following structure where the carboxylic acid group may be positioned at either the indicated 5 or 6 position,

LysoSensor™ Green DND-153 as represented by the following structure,

2',7'-difluorofluorescein (CAS #195136-58-4) as represented by the following structure, and, 2-{2-[-(tert-butyl-dimethyl-silanyloxy)-ethyl]-4-methoxy-phenyl}-4-phenyl-quinoline as represented by the following structure SNARF® is a registered trademark of Invitrogen, INC., 4849 Pitchford Avenue Eugene Oreg. 97402, for fluorescent dye used in scientific research to measure pH.

The above referenced compounds will fluoresce in response to an excitation source such as a mode locked light source, i.e. a UV LED or a blue LED or a mode locked laser that emits light radiation at wavelengths between about 325 nm and about 700 nm See column 16, lines 14-67 of U.S. Pat. No. 6,558,626. The entirety of U.S. Pat. No. 6,558,626 is incorporated herein by reference. In the preferred embodiment, the pH sensitive molecule along with a polymer material, such as but not limited to polyethylene, polyisobutylene, cellulose acetate, polystyrene, polyvinyl chloride, polydimethylsiloxane, and phenyl containing siloxane copolymers are spin-coated on the interior of a glass capillary. Thus, the method of the current invention is readily adaptable for use within the detector assembly described by U.S. Pat. No. 6,558,626.

Figure 1:
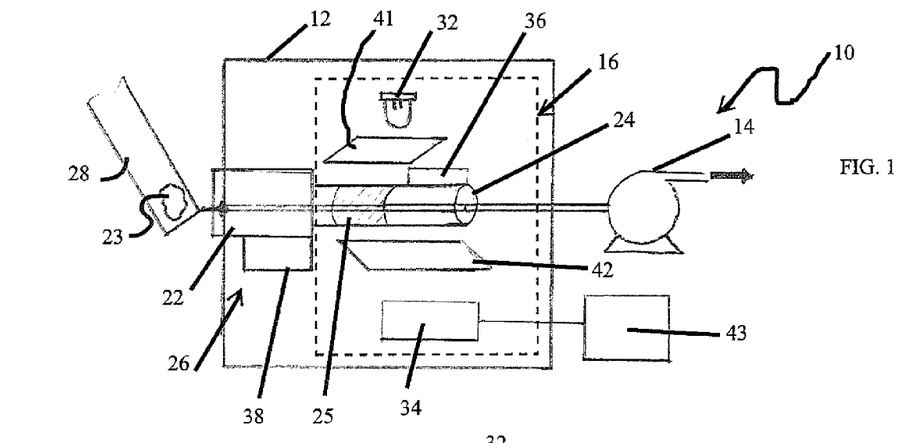
FIG. 1 provides a schematic view of one configuration of the current invention.
Figure 2:
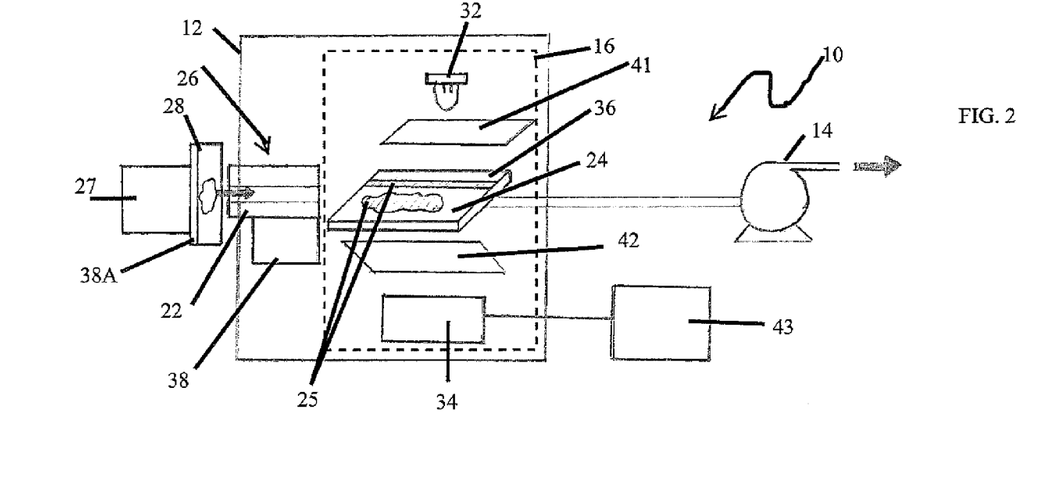
FIG. 2 provides a schematic view of an alternative configuration of the current invention.

With reference to FIGS. 1 and 2 and as discussed at column 3, lines 25-58 of the '626 patent, the detector assembly 10 comprises a housing 12, a gas movement pump 14 and a sensor assembly 16. Pump 14 provides the ability to move vapors from the tip or entrance 22 to the detector assembly and by the solid substrate 24 within the sensor assembly 16. Additionally, detector assembly 10 includes a heated tip assembly 26 which provides fluid communication between the exterior of the detector assembly housing 12 and ultimately to sensor assembly 16. Tip assembly 26 can be a bare heated inlet or even a sample desorber 27 that heats a sample collection material 28 without requiring the user to press said sample collection material 28 against the hot inlet tip 22.

Positioned within the sensor assembly is a short pass filter 41 located between the excitations source 32 and the solid substrate 24, a long pass filter 42 located between solid substrate 24 and the light detector 34 or suitable sensor. As known to those skilled in the art, short pass 41 and long pass 42 filters manage the wavelengths of radiation reaching substrate 24 and light sensor 34. Solid substrate 24, such as but not limited to a glass capillary, a flat plate of plastic, glass or other non-reactive support material carries the pH sensitive molecule 25 and optionally carries a hydrophobic polymer or plasticizers selected from, but not limited to, polyethylene, polyisobutylene, cellulose acetate, polystyrene, polyvinyl chloride, polydimethylsiloxane, and phenyl containing siloxane copolymers.

FIG. 1 schematically depicts a configuration utilizing a glass capillary as solid substrates 24 and FIG. 2 schematically depicts a configuration using a flat substrate as solid substrate 24. As depicted in FIG. 2, pH sensitive molecule 25 can be applied as a generic zone or as a continuous strip across the substrate. Detector assembly housing 12 is configured to provide fluid communication between solid substrate 24 and heated tip assembly 26. Sensor assembly 16 also includes the excitation source 32 and a light detector 34 or sensor suitable for detecting changes in response intensity of the pH sensitive molecule at wavelengths between about 325 nm and about 700 nm. Thus, sensor assembly 16 provides the ability to detect increases or decreases in response intensity of the pH sensitive molecule during excitation by the excitation source in response to the presence of an acid component of an oxidizing salt. Associated with sensor assembly 16 and light detector 34 is a display 43 suitable for displaying the response of light detector 34. Display 34 may be integral with detector assembly 10 or a separate component therefrom. Additionally, one skilled in the art will appreciate that control of detector assembly 10 will be managed by a properly programmed computer processor (not shown).

Sensor assembly 16 and tip assembly 26 each have associated heat sources 36 and 38. During the practice of the current invention, heat source 38 associated with tip assembly 26 maintains inlet tip 22 or sample desorber 27 operational temperature at a temperature sufficient to induce evaporative dissociation of the suspected analyte. For example, tip temperatures for ammonium nitrate will be between about 100° C. to about 170° C. Typically, tip temperature will be above 120° C. Generally, the tip operational temperature is from about 130° to about 170°. Note, sample desorber 27 may include its own heat source 38a thereby precluding the need to contact sample collection 28 directly against heated tip 22. Heat source 36 associated with sensor assembly 16 generally maintains the sensor assembly between about 25° C. to about 100° C. More typically, sensor assembly 16 will operate at a temperature between about 35° C. to about 85° C. with the most common operational temperature being about 45° C. to 70° C. At these temperatures, the flow rate of the vapors through sensor assembly 16 will preclude condensation. The preferred sensor assembly operating temperature maximizes performance of the pH sensitive molecule. The preferred operating temperature range will maximize fluorescent response and detection.

Optionally, the method of the current invention also includes establishing an initial response baseline also known as a controlled response for the pH sensitive molecule. To establish the baseline response for the pH sensitive molecule the user activates the excitation source and heaters allowing each to achieve operational conditions. Then the user presents the coated solid substrate 24, free of oxidizing salt, to detector assembly 16 producing a possible detectable response from the pH sensitive molecule. Thus, any response resulting from this process is free of influence from an acid component.

For example, a controlled response suitable for establishing a baseline can be produced from the pH sensitive molecule by presenting sample collection material 28 (e.g. swipe, vortexed air collection, wire mesh or wire screen) to the operating detector assembly. The response generated by the pH sensitive molecule to sample collection material 28 that is free of oxidizing salts is generally repeatable and predictable. Therefore, the result can be used to cancel out background noise in the sensor assembly. Background cancellation in the data analysis programming results in a cleaner real-time output display desired in product ready devices. The controlled response establishment step uses ambient conditions. Following the establishment of the controlled response, subsequent changes in response intensity from the pH sensitive molecule can then be attributed to the presence of a vapor phase acid component of an oxidizing salt in the gas passing through the detector assembly.

Following establishment of the baseline and heating the tip to the indicated range for the oxidizing salt suspected to be on the surface of interest. For example, when ammonium nitrated is suspected to be on the surface, the sampling tip assembly will be heated to a temperature between about 120° C. and about 170° C. When the tip assembly has reached the desired temperature, sample collection material 28 carrying collected trace amounts of an oxidizing salt 23 is presented to the tip assembly of the detector. Contact with the heated tip assembly induces evaporative dissociation of the oxidizing salt into its basic and acidic components. A pump pulls the vapor phase components into the detector and passes the components over the pH sensitive molecule. Upon reaction of the acidic component with pH sensitive molecule, the pH sensitive molecule situated upon a solid substrate will undergo a change in response intensity. The light sensor within the sensor assembly registers the change in response intensity of the pH sensitive molecule thereby establishing the presence of an oxidizing salt on the sampling material. In general, collecting and presenting about five to about 50 nanograms of oxidizing salt to the tip will generate a sufficient quantity of the acid component to produce a positive result.

Thus, exposure of oxidizing salts on the sampling material to the tip assembly operating at the indicated temperatures will induce evaporative dissociation releasing the detectable acid component of the salt. Oxidizing salts detectable by the disclosed process include urea nitrate, ammonium nitrate, ammonium perchlorate and guanidine nitrate. Additionally, the method of the present invention will detect the ammonium nitrate portion of ammonium nitrate/fuel oil mixtures.

During operation and detection, a pump within the detector pulls air in through the heated tip assembly passing it to the solid substrate carrying the pH sensitive molecule within the sensor assembly. Typically, this pump operates at a flow rate between about 10 $cm^3$/minute and about 200 $cm^3$/minute. More commonly, the flow rate through the sensor assembly will be between about 20 $cm^3$/minute and 60 $cm^3$/minute. In general, the flow rate is selected to ensure sufficient residence time of the acid component in the glass capillary and to preclude condensation of the vapor components within the detector assembly. Operation of the detector in the described manner will permit sensing of oxidizing salts on the sampling material as low as about 5 nanograms. Typically, response time from exposure of the oxidizing salt to the tip to a positive response ranges from less than one second up to about ten seconds.

Example 1

Detection of Ammonium Nitrate

Figure 3:
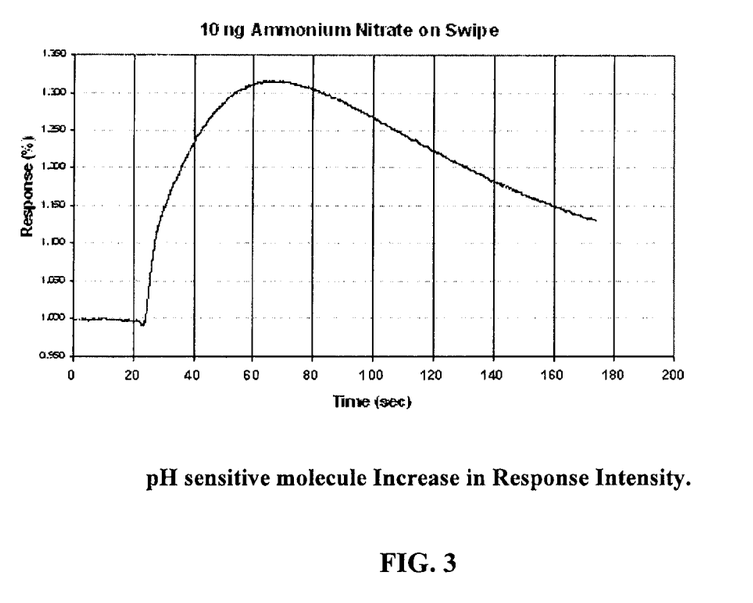
FIG. 3, depicts pH sensitive molecule increase in response intensity.

A response baseline for the pH sensitive molecule was established by sampling ambient air. A ten nanogram sample of ammonium nitrate was applied to a polytetrafluoroethylene swipe by pipetting a small volume of methanol solution. The swipe was placed in the flow path directly in front of the solid substrate, in this case, a glass capillary and then heated to 145° C. by contact with the hot inlet tip of the sensor. The glass capillary was spin-coated with 2-[5-methoxy-2-(4-phenyl-quinoline-2yl-phenyl]-ethanol combined with phenyl containing siloxane copolymers. A pump operating at 30 $cm^3$/minute was actuated and the evaporative dissociation products, in vapor form, were carried through the spin-coated capillary. The excitation source was a 405 nm source and the light sensor was a 435 nm long pass. As reflected in FIG. 3, under these conditions the pH sensitive molecule experienced a marked increase in response intensity over the established baseline.

The above testing method was repeated using polytetrafluoroethylene swipes carrying ammonium nitrate/fuel oil (ANFO) and swipes carrying urea nitrate. In each instance, the pH sensitive molecule underwent a detectable increase in response intensity. Using the above procedure, ANFO was detectable at a concentration of about 8 ng and urea nitrate at a concentration of about 5 ng. See Table 1. Based on the resulting increase in response, approximately 30% of the oxidizing salt in each sample underwent evaporative dissociation.

Example 2

Figure 4:
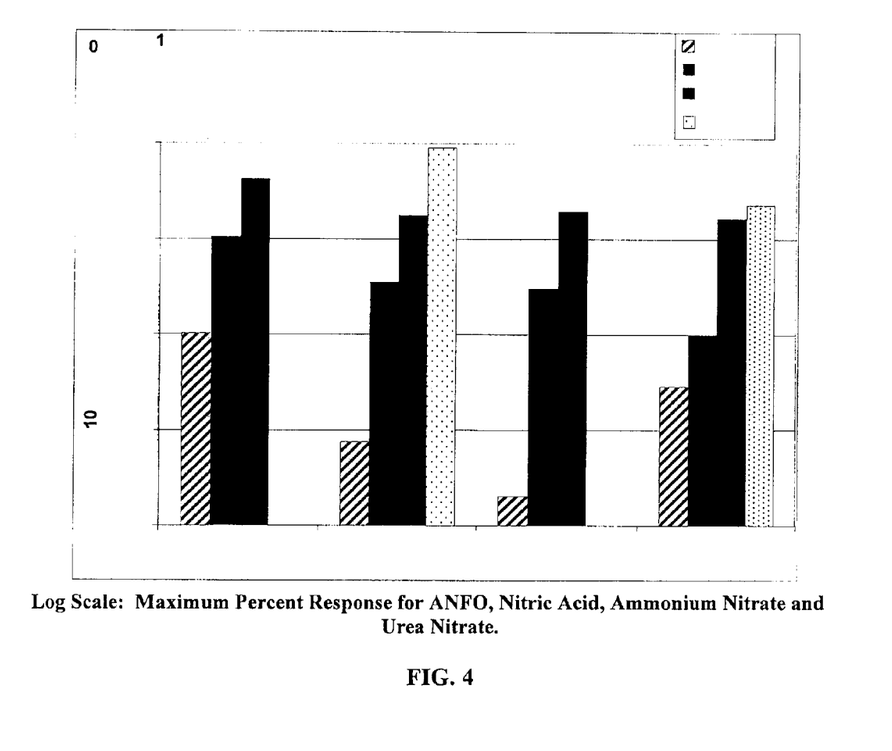
FIG. 4 depicts a log scale showing maximum percent response for ANFO, nitric acid, ammonium nitrate and urea nitrate.

A field test was performed where small amounts of dry ammonium nitrate (AN), urea nitrate (UN), and ANFO were fingerprint transferred (touch by hand and then transferred) to the surface of glass, plastics, cardboard and metals. A polytetrafluoroethylene swipe was dragged across each contaminated surface to transfer the powder to the swipe. The swipe was then presented to or inserted into a tip assembly in connection with a detector equipped with a pH sensitive molecule modified sensing element. The results shown in FIG. 4 and Table 1 depict the percent change in response intensity and compares to the same amount to nitric acid. Each test sample produced a positive response as reflected by the increased response intensity.

TABLE 1

Limits of detection (with 10% response intensity increase representing the lowest detectable response).

| Analyte | Mass Tested | Extrapolated Limit of Detection | Notes |
| --- | --- | --- | --- |
| Nitric acid | 1 ng | 1 ng | Measured 10% response intensity increase for 1 ng |
| Ammonium nitrate | 33 ng | 7.7 ng | Measured 43% average response intensity increase for ten 33 ng samples |
| Ammonium nitrate fuel oil | 1 ng, 10 ng | 7.7 ng | Measured 0.8% response intensity increase from 1 ng and 35% from 10 ng samples |
| Urea nitrate | 1 ng, 100 ng | 4.8 ng | Average 2.9% response intensity increase from 1 ng and 164% from 100 ng samples |

Example 3

The following example confirms the evaporative dissociation of nitric acid from ammonium nitrate. GC/MS techniques were used to identify the mass spectrum for nitric acid. Concentrated nitric acid was passed through a prepless sample introduction probe (PSI probe) and guard column setup on a 1200 L triple quadrupole instrument. The PSI-Probe allows solid materials to be introduced in the GC instead of injecting solutions. The spectrum for pure nitric acid revealed a base peak of 46 m/z with a small molecular ion peak at 63 m/z, approximately 1% of the height of the base peak where m/z is mass-to-charge ratio. In order to increase the molecular ion abundance and therefore increase the confidence in discriminating nitric acid from other analytes, thermal analysis was conducted on an ion trap GC/MS system utilizing methane chemical ionization. With this setup, the ratio of the nitric acid's protonated molecular ion, 64 mlz, to the 46 m/z base peak, was approximately 13%.

A small amount of ammonium nitrate was placed into the injector of the ion trap GC/MS instrument via a PSI probe. When the injector was heated to 150° C., $NO_2$ and nitric acid were both detected. The ratio of protonated molecular ion (64 m/z) to 46 m/z was much lower than the 13% observed for neat nitric acid, due to evolution of $NO_2$ in addition to nitric acid produced from ammonium nitrate by evaporative dissociation. The presence of nitric acid as a result of the evaporative dissociation of ammonium nitrate was still identifiable due to the presence of the protonated molecular ion peak occurring at 64 m/z. Thus, this test confirms that heating of ammonium nitrate evolves nitric acid ($NH_3$) nitric oxide (NO) and nitrogen dioxide ($NO_2$).

Example 4

The following example demonstrates that the fluorescent compounds do not respond to nitric oxide (NO). On a 1200 L triple quadrupole mass spectrometer, the system was setup with a 50/50 split configuration to deliver the effluent to both a sensor and the mass spectrometer concurrently. One side of the split configuration was directed to a sensor equipped with a preferred pH sensitive molecule coated sensing element. In order to produce NO, a small amount of 2,4,6-trinitrotoluene (TNT) was placed into the injector and pyrolyzed at 425 C.°, which immediately evolves NO gas (30 m/z).

The mass spectrometer detected the NO; however, the fluorescent sensor did not produce a detectable change in response intensity. Therefore, the pH sensitive molecule compound did not respond to the presence of NO.

Thus, the present invention is well adapted for the detection of oxidizing salts. While preferred embodiments of the invention have been described for the purpose of this disclosure, changes can be made by those skilled in the art without departing from the spirit and scope of the present invention. Thus, the true nature of the current invention is defined by the appended claims.

We claim:
1. A method for determining the presence of an oxidizing salt comprising:
   collecting the oxidizing salt with a sampling material;
   presenting the sampling material to a sensor assembly, said sensor assembly including a solid substrate carrying a pH sensitive molecule, the pH sensitive molecule undergoing stimulation by an excitation source, said excitation source emitting light radiation at wavelengths between about 325 nm and about 700 nm, while monitoring the response of the pH sensitive molecule to the stimulation with a light sensor suitable for detecting changes in response intensity;
   heating the sampling material to a temperature sufficient to induce evaporative dissociation of the oxidizing salt thereby yielding evaporative dissociation compounds of the oxidizing salt;
   passing the evaporative dissociation compounds of the oxidizing salt into said sensor assembly and reacting said pH sensitive molecule with at least one dissociation compound;
   monitoring said pH sensitive molecule with said light sensor to determine any change in response intensity wherein a change in response intensity indicates the presence of oxidizing salt.

2. The method of claim 1, wherein said pH sensitive molecule is selected from the group consisting of:
   SNARF®-5F, 5-(and-6)-carboxylic acid as represented by the following structure where the carboxylic acid group may be positioned at either the indicated 5 or 6 position,

SNARF®-4F, 5-(and-6)-carboxylic acid as represented by the following structure where the carboxylic acid group may be positioned at either the indicated 5 or 6 position,

5-(and-6)-carboxy SNARF®-1, as represented by the following structure where the carboxylic acid group may be positioned at either the indicated 5 or 6 position,

LysoSensor™ Green DND-153 as represented by the following structure,

2',7'-difluorofluorescein as represented by the following structure,

2-[5-methoxy-2-(4-phenyl-quinoline-2yl)-phenyl]-ethanol as represented by the following structure and, 2-{2-[-(tert-butyl-dimethyl-silanyloxy)-ethyl]-4-methoxy-phenyl}-4-phenyl-quinoline as represented by the following structure 3. The method of claim 1, wherein the sensor assembly operates at a temperature lower than the temperature required to induce evaporative dissociation of the oxidizing salt.

4. The method of claim 3, wherein the sensor assembly operates at a temperature between about 25° C. and about 100° C.

5. The method of claim 3, wherein the sensor assembly operates at a temperature between about 35° C. and about 85° C.

6. The method of claim 3, wherein the sensor assembly operates at a temperature between about 45° C. and about 70° C.

7. The method of claim 3, wherein the flow rate of vapors through the sensor assembly is sufficient to substantially preclude condensation of vapors on the interior of the sensor assembly.

8. The method of claim 3, wherein the flow rate of vapors through the sensor assembly is between about 10 cm³/minute and about 200 cm³/minute.

9. The method of claim 3, wherein the flow rate of vapors through the sensor assembly is between about 20 cm³/minute and about 60 cm³/minute.

10. The method of claim 1, wherein said sensor assembly includes a sample tip providing fluid communication between the interior and exterior of said sensor assembly and wherein said sample tip assembly is heated to the temperature sufficient to induce evaporative dissociation and further comprising the step of contacting said sample tip assembly with said sampling material thereby inducing evaporative dissociation of any oxidizing salt collected on said sampling material.

11. The method of claim 1, wherein the acid component of the evaporative dissociation compounds of the oxidizing salt released from the sampling material pass along said solid substrate, reacting with said pH sensitive molecule producing a change in response intensity detectable by the light sensor.

12. A method for determining the presence of oxidizing salt on a surface comprising:
contacting a surface suspected of carrying an oxidizing salt selected from the group consisting of ammonium nitrate, urea nitrate, guanidine nitrate and ammonium perchlorate with a sampling material thereby collecting a sample from said surface;
presenting the sampling material to a sensor assembly, said sensor assembly including a solid substrate carrying a pH sensitive molecule, the pH sensitive molecule undergoing stimulation by an excitation source, said excitation source emitting light radiation at wavelengths between about 325 nm and about 700 nm, while monitoring the response of the pH sensitive molecule to the stimulation with a light sensor suitable for detecting changes in response intensity;
heating the sampling material to a temperature sufficient to induce evaporative dissociation of the oxidizing salt thereby yielding evaporative dissociation compounds of ammonium nitrate;
passing the evaporative dissociation compounds into said sensor assembly and reacting said pH sensitive molecule with said dissociation compounds;
monitoring said pH sensitive molecule with said light sensor for a change in response intensity thereby indicating the presence of an oxidizing salt on the sampled surface.

13. The method of claim 12, wherein the step of heating the sampling material takes place at a temperature of about 100° C. to about 160° C. when the oxidizing salt is believed to be ammonium nitrate.

14. The method of claim 12, wherein the step of heating the sampling material takes place at a temperature of about 90° C. to about 120° C. when the oxidizing salt is believed to be urea nitrate.

15. The method of claim 12, wherein the step of heating the sampling material takes place at a temperature of about 210° C. to about 225° C. when the oxidizing salt is believed to be guanidine nitrate.

16. The method of claim 12, wherein the step of heating the sampling material takes place at a temperature of about 250° C. to about 350° C. when the oxidizing salt is believed to be ammonium perchlorate.

17. The method of claim 12, wherein said pH sensitive molecule is selected from the group consisting of:
SNARF®-5F, 5-(and-6)-carboxylic acid as represented by the following structure where the carboxylic acid group may be positioned at either the indicated 5 or 6 position,

SNARF®-4F, 5-(and-6)-carboxylic acid as represented by the following structure where the carboxylic acid group may be positioned at either the indicated 5 or 6 position,

5-(and-6)-carboxy SNARF®-1, as represented by the following structure where the carboxylic acid group may be positioned at either the indicated 5 or 6 position,

LysoSensor™ Green DND-153 as represented by the following structure,

2',7'-difluorofluorescein as represented by the following structure,

2-[5-methoxy-2-(4-phenyl-quinoline-2yl)-phenyl]-ethanol as represented by the following structure and, 2-{2-[-(tert-butyl-dimethyl-silanyloxy)-ethyl]-4-methoxy-phenyl}-4-phenyl-quinoline as represented by the following structure 18. The method of claim 12, wherein the sensor assembly operates at a temperature lower than the temperature required to induce evaporative dissociation of the oxidizing salt.

19. The method of claim 17, wherein the sensor assembly operates at a temperature between about 25° C. and about 100° C.

20. The method of claim 17, wherein the sensor assembly operates at a temperature between about 35° C. and about 85° C.

21. The method of claim 17, wherein the sensor assembly operates at a temperature between about 45° C. and about 70° C.

22. The method of claim 17, wherein the flow rate of vapors through the sensor assembly is sufficient to substantially preclude condensation of vapors on the interior of the sensor assembly.

23. The method of claim 17, wherein the flow rate of vapors through the sensor assembly is between about 10 $cm^3$/minute and about 200 $cm^3$/minute.

24. The method of claim 17, wherein the flow rate of vapors through the sensor assembly is between about 20 $cm^3$/minute and about 60 $cm^3$/minute.

25. The method of claim 12, wherein said sensor assembly includes a sample tip assembly providing fluid communication between the interior and exterior of said sensor assembly and wherein said sample tip assembly is heated to the temperature sufficient to induce evaporative dissociation and further comprising the step of contacting said sample tip with said sampling material thereby inducing evaporative dissociation of any oxidizing salt collected on said sampling material.

26. The method of claim 12, wherein the acid component of the evaporative dissociation compounds of the oxidizing salt released from the sampling material passes reacts with said pH sensitive molecule producing a change in response intensity detectable by the light sensor.

* * * * *